(12) United States Patent
Overturf et al.

(10) Patent No.: US 6,294,376 B1
(45) Date of Patent: Sep. 25, 2001

(54) CHOLESTEROL 7-ALPHA HYDROXYLASE EXPRESSION REGULATION

(76) Inventors: Merrill Overturf; David Loose-Mitchell, both of 6431 Fannin St., Houston, TX (US) 77225

(*) Notice: Subject to any disclaimer, the term of this patent is extended or adjusted under 35 U.S.C. 154(b) by 0 days.

(21) Appl. No.: 08/192,271

(22) Filed: Feb. 4, 1994

Related U.S. Application Data

(63) Continuation-in-part of application No. 08/014,828, filed on Feb. 5, 1993, now abandoned, which is a continuation-in-part of application No. 08/014,945, filed on Feb. 5, 1993, now abandoned.

(51) Int. Cl.$^7$ .................................................... C12N 15/00
(52) U.S. Cl. ........................ 435/320.1; 435/325; 536/24.1
(58) Field of Search ................................. 435/7.1, 252.3, 435/240.1, 240.2, 325, 320.1; 530/350; 514/12; 536/24.1

(56) References Cited

PUBLICATIONS

Cohen et al, Genomics 14: 153 (1991).*
Critical Synergy: The Biotechnology Industry and Intellectual Property Protection, Biotechnology Industry Organization, Oct. 17, 1994, pp. 75 and 100–107.*

* cited by examiner

Primary Examiner—James Martinell
(74) Attorney, Agent, or Firm—Martin L. McGregor

(57) ABSTRACT

A method for controlling cholesterol is provided. A cholesterol 7-alpha-hydroxylase (C7αH) regulatory factor is administered to control cholesterol catabolism. Also provided is a method for producing the cholesterol control agent and a nucleotide sequence involved in regulatory control.

6 Claims, 8 Drawing Sheets

FIGURE 3

SCREENING/PRIMER EXTENSION OLIGONUCLEOTIDE

RAB84/128 (SEQ ID NO: 7) 5' TAG TCC CAG AAT AAG CCA CAA ACA
ACA GCA CAC TGA TAG ACA TAT 3'

45MER αSENSE
PARTIAL RABBIT cDNA  84-128bp
TM = 72.7°C

FIGURE 4

SEQUENCE OF RESISTANT RABBIT 7-ALPHA HYDROXYLASE PROMOTER
SEQ ID NO: 8

```
1    atattttaag tttcattttt tccctgagtt ttttttgttg aagtattgca
atatgtgtgt
61   gtgtgtgtgt gtaataagaa tgtatacatc tccagagcat gatactactg
cccttcaaac
121  ccacaaagtc tttaatataa cctcatattt gtgcatgtgt ttatatgtca
gtcatctaac 181  cccgtgttgt cagattcagg ggtcattttt gatcctctta
cttgacctcg gagtagcatg
241  tgatatagtt cactcatctt ccttctgctc tggctttctg taccatgata
tcatctgcat
301  tttcttcctg actctcatta tcttcctcct caccttggac tgatctcccc
gagtgaagtg
361  tctgtggcct gggttgaatt ctgtttcttt ctttgatctt tctttctccc
taagtgattt
421  cataggacct cttggcttta aataccatcc aaatgctggt gaattgatat
ttatatctcc
481  aactctagcc tttctccttc actttagact cactcaattg tcaacttgac
attgacccga
541  tggttcctaa aagatctccc aaacatcata tgtccaaaat agtattctga
tgtattgcct
601  tccaagacct ctctccctgc tcacaagcaa ttctgtatga attgtttctt
atctaacttt
661  ttgtggtttt aatcttaggt aactttgtcg gattcactct gctccagtta
gttgtactaa
721  attttccagt tagtagatgt acaaagttta tgtttgaaat gaggtgggtt
tctttaataa
781  atagaaaaat taataaacaa atttaaggta taaaaaagtt tgataatgtt
tttatgctta
841  aaagaaactg ttttatttac tttcttgata ctaggtgagt aatatgttat
gatctatgta
901  aattgtctat gattttggaa aaatactgag acttgaagca agagaatcta
gttctcttcc
961  ctttgaactt aaccattgga tctctctggc atttaaatta atttcttctt
caaaatgtaa
1021 taagataaaa aaagcaacaa gatcaaatca ctagtttgat gaataattta
tacttagttt
1081 tctttatgtg ttacatattt actacatatg ttcatcttga acagatttgt
ttttatacac
1141 ataccaaact tgtaatacta gctgctgtcc ccaggaatga atgttgagtc
aacatatgtt
1201 tgagagacct tcaacttatc aagtattgca ggtttctgat tgttttggaa
gatcttctga
1261 tgcctgtgga cttagttcaa ggctagttaa taccactatc tttttttttcc
taataggatg
1321 aacaaatggt taattgtttg ctttggtcac tcaagttcaa gttattgaat
cagggtccta
```

FIGURE 4A 1381 cgtatataaa aactctagct tcagactgtt cagagacacc cttgcctttc taatcataga
1441 ttctccctgt caggagtttt acagatttgc gaaatgatta ccatatttgg atctggggga
1501 tatgtctatc agtgtgctgt tgtttgtggc ttattctggg actaaggaga aggtaaggaa
1561 agttttgttt atgttaaatt acctttagt tgtttcattt aatgttcttt ttcctctact
1621 gtataataag tttggtttcc catacttaca tatatctgca ttttcttctt cattttaaac
1681 tactgatttc attcaaacaa attgatatat tttgactata acaaagcatt tggcaggttc
1741 cttttttaaa attgacatat actaatgtaa tgtataaatg tgtacatttg ttaactatga
1801 ttgatggaaa tttcataaga tccctgtatg tgtttacgtg tctatgtaca aaaaaagctc
1861 ggattaggaa ggatcc

FIGURE 5

PARTIAL SEQUENCE OF RESISTANT RABBIT 7-ALPHA HYDROXYLASE PROMOTER
SEQ ID NO: 1

```
  1    GATAATACCA CTATCTTTTT TTTCCTAATA GGATGAACAC ATGGTTAATT
 51    GTTTGCTTTG GTCACTCAAG TTCAAGTTAT TGAATCAGGG TCCTACGTAT
101    ATAAAAACTC TAGCTTCAGA CTGTTCAGAG ACACCCTTGC CTTTCTAATC
151    ATAGATTCTC CCTGTCAGGA GTTTTACAGA TTTGCGAAAT GATTACCATA
201    TTTTGGATCT GGGGGGG
```

Expression of Rabbit Cholesterol 7α-Hydroxylase
in Human Hepatoma Cells

Figure 7

```
ALIGNMENT OF:

CRT RABBIT C7aH Promoter       216 BASES

VERSUS.

HUMAN C7aH Promoter            201 BASES (Spliced)

K-tuple size=  3
Window size=  20
Gap penalty=  7

Note start site of transcription is penultimate base in the human sequence
(base 1541), which corresponds to base 129 in the CRT sequence.
```

```
caacttatcaagtattgcaggtctctgattgctttggaaccacttctgatacctgtggac
x    1350      1360      1370      1380      1390 x       10        20        30        40
         GATATACCACTATCTTTTTTTTCCTAATAGGATGAACACATGGTTAAT
         : :        ::::::::  :::::::  :::::::  ::::  ::::
ttagttcaaggccagttactaccactttttttttctaatagaatgaacaaatggctaat
   1410      1420      1430      1440      1450

50        60        70        80        90       100
TGTTTGCTTTGGTCACTCAAGTTCAAGTTATTGAATCACGGTCCTACGTATATAAAAACT
::::::::::  :::   ::::  :::::::::      :::  ::: ::::::::::::
tgtttgctttg-tcaaccaagctcaagttaatggatctggatactatgtatataaaaagc
   1470      1480      1490      1500      1510

110       120       130       140       150       160
CTAGCTTCAGACTGTTCAGAGACACCCTTGCCTTTCTAATCATAGATTCTCCCTGTCAGG
:: :::::
ctagcttgagtctctttcagt
   1530        x 170       180       190       200       210   x
AGTTTTACAGATTTGCGAAATGATTACCATATTTTTGATCTCGGGGGG
```

```
NUMBER OF MATCHED BASES=43

83/201 = 41%
```

CHOLESTEROL 7-ALPHA HYDROXYLASE EXPRESSION REGULATION

RELATED APPLICATIONS

This application is a continuation in part of application Ser. Nos. 08/014,828, now abandoned and 08/014,945, now abandoned, both filed Feb. 5, 1993.

FIELD OF THE INVENTION

This invention relates to an agent(s) for controlling cholesterol in animals and to a method for using the agent(s) for controlling cholesterol in humans and other mammals. The agents of this invention promote the conversion of cholesterol to bile acids. In a preferred embodiment, an agent for increasing conversion of cholesterol to bile acids is provided. In one embodiment, a cholesterol 7-alpha-hydroxylase (C7αH) regulatory factor is administered to control cholesterol catabolism. In another embodiment, a method for stimulating bile acid excretion is provided. In another preferred embodiment, a method of treating and/or preventing atherosclerosis is provided. In another embodiment, a method for assessing the risk of developing hypercholesterolemia and/or atherosclerosis is provided.

BACKGROUND OF THE INVENTION

Arteriosclerosis, which literally means "hardening of the arteries," actually refers to a group of disorders which involves a thickening and loss of arterial elasticity. Although they frequently occur together, each of the principal disorders (Monckeberg's medial calcific sclerosis, arteriolosclerosis, and atherosclerosis) are distinguishable by the afflicted artery's morphological appearance. Monckeberg's medial calcific sclerosis is characterized by ringlike calcifications in small to medium sized arteries. Arteriolosclerosis is characterized by a thickening of artery and arteriole walls, resulting in lumen narrowing.

The predominant and most serious form of arteriosclerosis is atherosclerosis. In Western countries, atherosclerosis is responsible for 20% to 25% of myocardial infarction deaths yearly, and is a contributing factor in about 50% of deaths from all other causes. Atherosclerosis is also the major cause of a large number of morbidities, including chronic ischemic heart disease, gangrene, mesenteric occlusion, and ischemic encephalopathy.

Atherosclerosis is believed to begin in childhood as a progressive disease that first strikes the large- and medium-sized arteries. These include the coronary, the carotid, the aorta, and the larger arteries of the lower extremities. Later in life, lesions called "atheromas" or "fibrofatty plaques" form on the arterial inner walls. These plaques have a central necrotic core of lipid deposits composed primarily of cholesterol, calcium, cellular debris, and other materials. As the disease progresses, plaques coalesce, forming large masses, or what have been called "complicated plaques," in which there may be associated arterial calcification. Fatty streaks appear on the vessel walls, causing them to ulcerate and rupture. Debris (such as cholesterol emboli) are then released into the bloodstream. Hemorrhaging may occur from rupture of the overlying capillary endothelium. Eventually, clotting may occur within the vessel, causing tissue infarction.

The major risk factors associated with heart disease include hypercholesterolemia, hypertension, hyperglycemia and smoking. Hypercholesterolemia (high serum cholesterol) is present most of the time, and serum cholesterol concentrations correlate with mortality. The death rate from cardiac disease is three times greater in men with serum cholesterol concentrations greater than about 200 milligrams per deciliter (mg/dl) as compared to individuals having lower cholesterol concentrations in the same age groups.

There is a direct link between hypercholesterolemia and the incidence of complicated plaque formation and atherosclerosis. Atherosclerotic plaques are rich in cholesterol, particularly cholesterol esters. Experimental animals fed diets high in cholesterol or that have genetic disorders which produce high plasma cholesterol levels develop full-blown atherosclerosis. In humans, it is clear that a direct relationship exists between plasma cholesterol concentrations and mortality. Individuals who consume a diet rich in cholesterol and saturated fat have elevated plasma cholesterol concentrations and a higher incidence of atherosclerosis. Conversely, high risk individuals who take cholesterol-lowering drugs and restrict cholesterol intake have a lower incidence of cardiovascular mortality.

All plasma lipids, including cholesterol and triglyceride, circulate through the bloodstream in association with proteins. The major cholesterol- and triglyceride-carrying proteins are a group of lipoproteins collectively referred to as apoproteins. Coupled with lipid cargo, these lipoprotein complexes are classified according to their flotation constants or densities. Some of the major lipoprotein complexes include high density lipoprotein (HDL), intermediate density lipoprotein (IDL), low density lipoprotein (LDL), very low density lipoprotein (VLDL), and chylomicron. LDLs carry the primary plasma cholesterol load, and high amounts of the LDLs and plasma triglycerides are associated with an increased risk of atherosclerosis and related cardiovascular diseases.

Humans need only small amounts of cholesterol. Most cholesterol is produced in the liver, the only organ capable of breaking down and excreting excess cholesterol. The body's capacity to break down and rid itself of excess cholesterol is limited.

Excess cholesterol is carried by lipoprotein particles. These cholesterol-laden particles find small cracks in arterial walls, and initiate a process leading to fatty fibrous plaque buildup and arterial lumen obstruction. In coronary artery disease, lumen obstruction restricts blood flow. Lack of oxygen and other nutrients leads to cardiac muscle necrosis.

Coronary artery disease is the most common cause of death in the United States. Approximately thirty million people suffer from coronary artery disease, and nearly one million die from it each year.

Recent studies suggest a link between serum cholesterol reduction and arterial plaque reversal. The 1987 Cholesterol Lowering Atherosclerosis Study (CLAS) showed arterial plaque reversal in 16% of treated subjects as compared to 2% of placebo subjects. The treated subjects were given a combination of first-generation cholesterol control agents. Disease progression continued in 39% of the treated group and in 60% of the placebo group.

Presently, 85% of the cholesterol control agent market is covered by a class of drugs known as HMG Co-A reductase inhibitors. These drugs inhibit hepatic cholesterol synthesis. However, they have no effect on dietary cholesterol. All classes of cholesterol-lowering drugs are indicated for therapeutic use in familial hypercholesterolemia, a disorder that affects less than 1.5% of the population. All require a strict dietary regimen to achieve a significant lipid-lowering effect. These drugs may cause unwarranted side effects and have significant contra-indications. Side effects include rhabdomyolysis, myopathy, cataracts, and lupus erythematosus. Drug use is contraindicated in pregnancy and in liver disease.

For these reasons, the FDA and many clinicians have been reluctant to support the use of these agents for atherosclerosis prophylaxis (prevention), even in "high-risk" (Group I) patients, such as post-coronary bypass subjects. This attitude is changing however, and more physicians are treating "potentially high risk" (Group II) patients with cholesterol control agents. Therapeutic intervention could also be helpful as a prophylactic in "low risk" (Group III) individuals.

Several large population studies are being conducted with cholesterol synthesis control agents. The Healthy Heart Study in the United Kingdom will recruit eighteen thousand patients from general practitioners across the country. Over the next five years, some individuals will be given cholesterol synthesis lowering agents, and some individuals will be given placebos. The chief aim of this study is to determine the effects of cholesterol on mortality rates in a large population. The West of Scotland Coronary Prevention Study (WOSCOPS) will evaluate the effects of PRAVASTATIN on coronary artery disease in six thousand men.

These studies will establish the precedent for using cholesterol-lowering agents prophylactically. By treating Group III "low risk" individuals, the number of potential users in the U.S. could reach seventy to eighty million people by the end of the decade. Treatment of low risk populations in Europe, Latin America and the Orient could increase use to two hundred million people worldwide.

The cholesterol pool in an organism is primarily derived from two sources: 1) absorption of dietary cholesterol and 2) de novo synthesis. The size of the cholesterol pool can be decreased by restricting synthesis, restricting dietary intake, or excreting cholesterol through its conversion to bile acids. As discussed above, the prior art describes several agents for decreasing de novo cholesterol synthesis. Usually, reduction of dietary cholesterol is also required to achieve the desired plasma cholesterol levels.

An alternative strategy is to increase the body's ability to excrete cholesterol by converting cholesterol to bile acids. This method has the advantage of lowering serum cholesterol concentrations, irrespective of cholesterol origin (diet or synthesis). Thus, strict low-cholesterol diets may not be required if cholesterol can be effectively removed. Elimination of cholesterol by its conversion to bile acids also avoids any undesired effects associated with inhibiting steroid synthesis. However, in humans, rabbits, and other animals that develop hypercholesterolemia, cholesterol and oxysteroids inhibit cholesterol conversion to bile acids. Thus, serum cholesterol concentrations increase.

Molowa, D. T., et al., "Transcriptional regulation of the human cholesterol 7 alpha-hydroxylase gene," *Biochemistry* 31:2539–2544 (1992) and Takiguchi, Japanese Patent Application No. W092/00088 report non-specific proteins that stimulate bile acid production. However, the known methods for increasing bile acid production lack specificity and are known to affect other enzyme systems. The prior art does not disclose a specific agent which increases conversion of cholesterol to bile acids without affecting other enzyme systems.

Primary bile acids are synthesized in hepatocytes directly from cholesterol. The major bile acids in humans and some other mammals are cholic acid and chenodeoxycholic acid. Primary bile acids are often conjugated with glycine or taurine to form glycocholic or taurocholic acids, respectively. Primary bile acids undergo metabolism by intestinal flora to secondary bile acids such as deoxycholic and lithocholic acid.

Bile acids play a significant role in cholesterol metabolism. They represent the most significant pathway by which cholesterol and similar compounds bearing a steroid ring structure are excreted. In bile, bile acids prevent the precipitation of cholesterol and similar compounds in the gallbladder. Bile acids act as emulsifying agents and have a role in preparing triglycerides for lipase cleavage. Bile acids also facilitate absorption of fat-soluble vitamins across the digestive tract.

The rate limiting step in conversion of cholesterol to bile acids involves hydroxylation of carbon number 7 by cholesterol 7-alpha-hydroxylase (EC 1.14.13.17) ("C7αH"), which comprises a microsomal monooxygenase cytochrome P-450$_{C7αH}$ and a NADPH-cytochrome P-450 reductase. Cholesterol elimination through this pathway is important in controlling disorders such as, but not limited to, arteriosclerosis, hyperlipidemia, hypercholesterolemia, gallstone disease, and lipid storage diseases.

The cloning of a cDNA encoding human cytochrome P-450$_{C7αH}$ was disclosed in Noshiro, M. and Okuda, K., "Molecular cloning and sequence analysis of cDNA encoding human cholestersol 7 alpha-hydroxylase," *FEBS* 268:137–140 (1990), and the gene for rat C7αH in Nishimoto, M., et al., "Structural analysis of the gene encoding rat cholestersol alpha-hydroxylase, the key enzyme for bile acid synthesis," *J. Biol. Chem.* 266:6467–6469 (1991). Jelinek, D. F., et al., *J. Biol. Chem.* 265:8190–8197 (1990), and Li, Y. C., et al., "Regulation of cholesterol 7 alpha-hydroxylase in the liver. Cloning, sequencing and regulation of cholesterol 7 alpha-hydroxylase mRNA," *J. Biol. Chem.* 265:12012–12019 (1990) also disclose C7αH cDNA sequences. However, none of these references disclose the particular nucleotide sequence taught in the present invention, nor do they disclose specific regulatory factors which control expression of C7αH (C7αH regulatory factor) or related factors for controlling cholesterol or other steroids. Molowa, D. T., et al., "Transcriptional regulation of the human cholesterol 7 alpha-hydroxylase gene," *Biochemistry* 31:2539–2544 (1992), suggest that hepatocyte nuclear factor-3 ("HNF-3") may be involved in the control of C7αH expression. However, the C7αH regulatory factors of the present invention are not the HNF-3 factors of Molowa, D. T., et al., as shown in Example 7, below.

The prior art provides no mechanism for avoiding the inhibition of C7αH expression by increased levels of cholesterol which occurs in species susceptible to hyperlipidemia and atherosclerosis. The art does not teach a C7αH promoter sequence which interacts with a regulatory factor specifically regulating C7αH expression in a manner that reduces the inhibition of cholesterol conversion to bile acids by increased cholesterol concentrations. These and other shortcomings of the prior art are overcome by the present invention as described below.

SUMMARY OF THE INVENTION

In the present invention, we provide a genomic DNA library previously unavailable to the public. The genomic DNA library codes for a C7αH regulatory factor which interacts with the C7αH core promoter DNA sequence and increases the conversion of cholesterol to bile acids.

It is an object of the present invention to provide a C7αH regulatory factor which interacts with the DNA sequence of the C7αH core promoter, or with sequences having substantial homology with the C7αH core promoter, or mixtures thereof, resulting in increased C7αH mRNA expression while avoiding or reducing cholesterol-induced inhibition of cholesterol conversion to bile acids.

It is a further object of the present invention to provide a method for controlling hypercholesterolemia, which comprises administering a C7αH regulatory factor which increases the expression of a cholesterol catabolizing enzyme, preferably the C7αH enzyme, and avoiding inhibition of cholesterol conversion to bile acids in the presence of cholesterol.

It is also an object of the present invention to provide a C7αH regulatory factor which increases production of bile acids that is characterized by interacting with the C7αH core promoter leading to increased conversion of cholesterol to bile acids, and is not subject to inhibition by cholesterol.

It is an object of this invention to provide a genomic library which contains the C7αH core promoter sequence and, when expressed, provides the C7αH regulatory factor.

It is an object of the present invention to provide a DNA fragment comprising the sequence of the C7αH core promoter, or a fragment having substantial homology with the sequence of the C7αH core promoter, or mixtures thereof, having the sequence of SEQ ID NO: 8, which is useful in identifying and purifying the C7αH regulatory factor.

It is an object of the present invention to provide a transformed cell comprising the DNA sequence of the C7αH core promoter, or a fragment having substantial homology with the sequence of the C7αH core promoter, or mixtures thereof, having the sequence of SEQ ID NO: 8.

It is an object of the present invention to provide a vector comprising the DNA sequence of the C7αH core promoter, or a fragment having substantial homology with the sequence of the C7αH core promoter, or mixtures thereof, having the sequence of SEQ ID NO: 8.

It is a further object of the invention to provide a method for controlling hypercholesterolemia by controlling the transcription of the cholesterol 7-alpha hydroxylase gene and converting cholesterol to bile acids while avoiding inhibition by cholesterol.

It is also an object of the present invention to provide a method for assessing the risk of developing atherosclerosis, comprising measuring the level of a C7αH regulatory factor directly or indirectly by measuring a linked parameter such as C7αH mRNA levels.

These and other objects and advantages of the present invention will become apparent from the following detailed description.

DESCRIPTION OF THE DRAWINGS

FIG. 3. Sequence of the screening oligonucleotide corresponding to rabbit C7αH sequence in Exon 1 at nucleotides 84–129.

FIGS. 4 and 4A. DNA sequence of the C7αH promoter region of the rabbit.

FIG. 5. Partial DNA sequence of the C7αH promoter region of the rabbit.

FIG. 7. Comparison of the sequences of the rabbit and human C7αH core promoter.

DETAILED DESCRIPTION OF THE INVENTION

Figure 1:
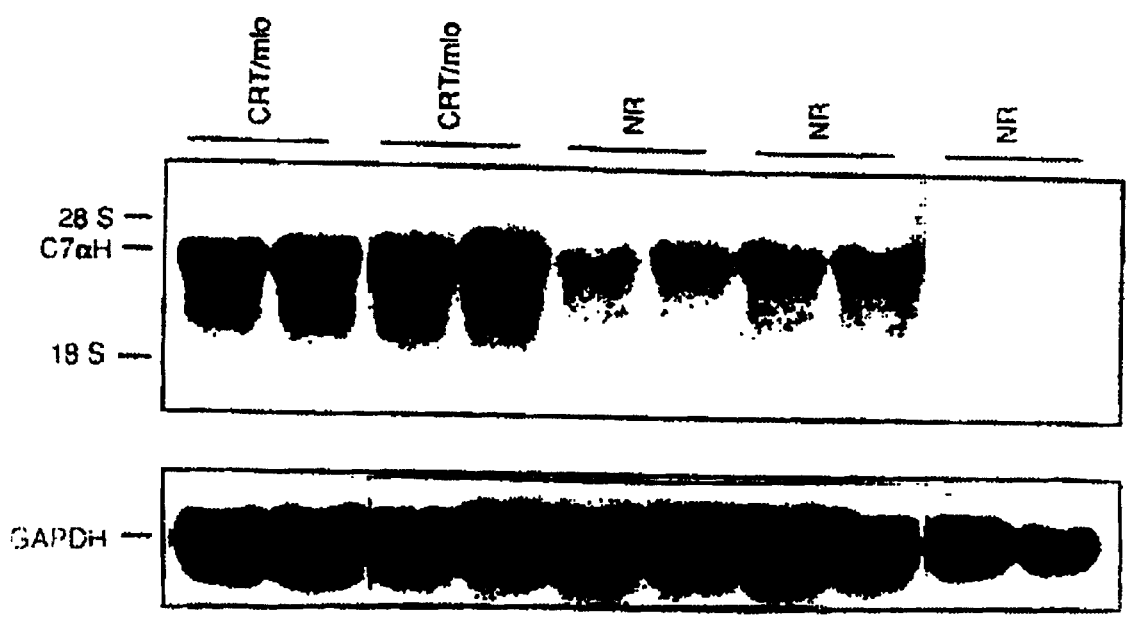
FIG. 1. RNA-blot of total hepatic mRNA from representative resistant (CRT) and normal (NR) rabbits fed a basal, low-cholesterol diet.

The typical New Zealand white rabbit responds to a high-cholesterol diet by developing hypercholesterolemia, as do many other mammals, including humans.

We have developed and characterized a colony of New Zealand white rabbits (hereinafter the "CRT" rabbit) which are resistant to the hypercholesterolemia that typically results from a high-cholesterol diet. A 0.1% cholesterol-enriched diet fed to normal rabbits ("NR") results in plasma cholesterol concentrations of approximately 330 mg/dl after a period of about eight weeks. Under the same dietary conditions, the CRT rabbits maintain plasma cholesterol concentrations of less than 50 mg/dl. The CRT phenotype is defined as an elevation in plasma cholesterol concentration greater than or equal to 1.5 standard deviations (SD) below the mean plasma cholesterol concentration of NR rabbits, at both four and eight weeks, who have consumed a 0.1% cholesterol-enriched diet. The phenotype of the CRT rabbit is inheritable, as described in the following references: 1) Overturf, M. L., Smith, S. A., Hewett-Emmett, D., Loose-Mitchell, D. S., Soma, M. R., Gotto, Jr., A. M. and Morrisett, J. D., "Development and Partial Metabolic Characterization of a Dietary Cholesterol-Resistant Colony of Rabbits," *J. Lipid Res.* 30:263–273 (1989); 2) Soma, M. R., Morrisett, J. D., Gotto, Jr., A. M., Loose-Mitchell, D. S., Poorman, J. A., Smith, S. A. and Overturf, M. L. "Cholesterol Metabolism in Fibroblasts from Rabbits Resistant to Dietary-Induced Hypercholesterolemia," *J. Lipid Res.* 31:985–994 (1990); 3) Overturf, M. L., Smith, S. A., Gotto, Jr., A. M., Morrisett, J. D., Tewson, T., Poorman, J. A. and Loose-Mitchell, D. S. "Dietary Cholesterol Absorption, and Sterol and Bile Acid Excretion in Hypercholesterolemia-Resistant White Rabbits," *J. Lipid Res.* 31:2019–2027 (1990); and 4) Loose-Mitchell, D. S., Poorman, J. A., Smith, S. A., Overturf, M. L., Morrisett, J. D., Gotto, Jr., A. M. and Soma, M. R. "Hepatic Cholesterol Metabolism in Hypercholesterolemia-Resistant Rabbits," *Atherosclerosis* 87:169–181 (1991). The cDNA sequences for the C7αH gene of the normal and CRT rabbit are described in the doctoral dissertation of J. A. Poorman, "Altered Cholesterol Metabolism in a Hypercholesterolemia Resistant Rabbit Colony," University of Texas Health Science Center at Houston Graduate School of Biomedical Sciences, May 1991. Poorman found the C7αH cDNA's to be substantially the same in NR and CRT animals.

In all species investigated to date, substantial variations have been observed in plasma cholesterol concentrations following dietary cholesterol challenge. This variation extends from cases wherein individuals develop little or no increase in plasma cholesterol to cases wherein individuals develop severe hypercholesterolemia. However, in the CRT strain, we have observed an alteration in cholesterol metabolism that eliminates excess cholesterol, even in the presence of high levels of dietary cholesterol. In the present invention, we now provide a genomic DNA library of the mlo/CRT phenotype, previously unavailable to the public. The genomic DNA library provides DNA that codes for a C7αH regulatory factor which interacts with the C7αH core promoter and increases cholesterol conversion to bile acids in the presence of dietary cholesterol. We also provide the core promoter DNA sequence useful for identifying the C7αH regulatory factor that increases cholesterol conversion to bile acids, even in the presence of cholesterol. The C7αH regulatory factor can be obtained by expression of the genomic DNA library and isolated by its interaction with the DNA core promoter sequence of this invention.

The C7αH regulatory factor is used to control hypercholesterolemia. The C7αH regulatory factor of the present invention occurs in combination with increased C7αH mRNA and maintains cholesterol to bile acid conversion, even in the presence of cholesterol. In animals that develop hypercholesterolemia (such as NR rabbits), C7αH mRNA levels are lower, and bile acid production decreases as serum cholesterol concentrations increase. The cholesterol regulatory factor of this invention interacts with the core promoter sequence of the CRT rabbit and results in increased C7αH mRNA levels in the ranges of about 1.25 fold to about 90 fold. The CRT C7αH regulatory factor can be used to increase conversion of cholesterol to bile acids, even in the presence of dietary cholesterol.

The C7αH regulatory factor isolated as described in Examples 6 or 7 below, may be compounded with suitable carriers known to those skilled in the art as acceptable for delivery of agents similar to the C7αH regulatory factor. The nature of these carriers is predicated on the chemical nature of the C7αH regulatory factor, as would be determined by a person having ordinary skill in the art. The dosage will be sufficient to provide an increase in C7αH mRNA levels of from about 1.25 to about 90 fold, preferably about 2.0 to about 25 fold, more preferably from about 5 to about 10 fold. Alternatively, the dosage is varied to control hypercholesterolemia such as, but not limited to, achieving a desired serum cholesterol level, preferably less than about 250 mg/dl, and more preferably less than about 200 mg/dl in animals such as, but not limited to, humans.

The C7αH regulatory factor may be administered to animals such as, but not limited to, humans. The C7αH regulatory factor may be administered to those individuals at high (Group I) or moderate (Group II) risk of developing hypercholesterolemia and/or coronary artery disease. The C7αH regulatory factor may also be administered prophylactically to individuals at low risk (Group III) to prevent the onset of hypercholesterolemia and/or coronary artery disease. The C7αH regulatory factor may be administered by mechanisms which deliver it to tissues which regulate the expression of cholesterol metabolizing enzyme(s). Delivery may be orally, rectally, transdermally, via implant, intranasally, by injection or otherwise made available. Thus, the C7αH regulatory factor is useful in a method of controlling hypercholesterolemia by administering the C7αH regulatory factor in a dose effective to maintain a desired level of cholesterol, particularly serum cholesterol.

Alternatively, hypercholesterolemia in an individual may be controlled by administering to the individual a DNA fragment which has a C7αH core promoter sequence, the human C7αH gene and a sequence which codes for a C7αH regulatory factor in a system which decreases the inhibition of C7αH activity by cholesterol. The sequences may be administered by transfection, or other means that permit the sequences to be expressed and function to increase conversion of cholesterol to one or more bile acids.

The sequence that codes for the C7αH regulatory factor may be used as a diagnostic tool for assessing risk of developing hypercholesterolemia and/or coronary artery disease. The DNA sequence coding for the C7αH regulatory region may be isolated and compared to the sequence found in normal and/or at-risk individuals. In the diagnostic assay, "at-risk" individuals are those who have or may develop hypercholesterolemia and/or coronary artery disease. The methods for isolating and comparing regulatory gene sequences are well known in the art. In an alternate embodiment, the sequence coding for the C7αH regulatory factor that binds to the sequence of FIG. 4 may be analyzed and compared to the sequence found in normal and/or at-risk individuals. Also, the regulatory factor that binds to the sequence of FIGS. 4 and 4A may be analyzed and compared to the sequence found in normal and/or at-risk individuals. These include, but are not limited to sequences linked upstream (i.e., in the 5' direction) to the sequence of FIGS. 4 and 4A.

Alternatively, the C7αH regulatory factor may be used in a diagnostic assay. The C7αH regulatory factor may be measured in tissue and/or body fluids using standard analytical techniques. The DNA sequence of FIGS. 4 and 4A, SEQ ID NO: 8 and the partial sequence of FIG. 5, SEQ ID NO: 1 is useful in identifying and isolating the C7αH expression regulatory factor. The sequences are also useful in identifying rabbit tissue, as the sequence is a unique characteristic of rabbit tissue.

Figure 6:
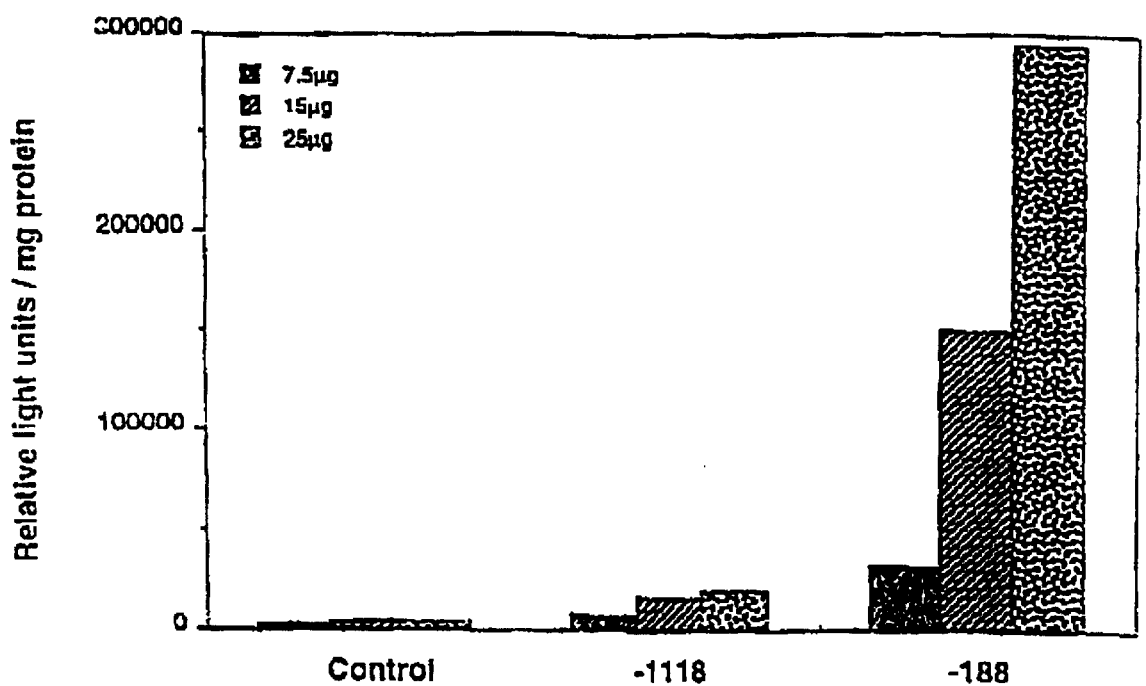
FIG. 6. Expression of rabbit cholesterol 7α-hydroxylase in human hepatoma cells.

The rabbit core promoter sequences of SEQ ID NO: 8 and SEQ ID NO: 1 have been shown to promote expression of downstream genes in human hepatocytes as further described in Example 11 infra. The results are illustrated in FIG. 6.

The terms and phrases as used herein have the following meanings:

a). "Controlling hypercholesterolemia" is defined as a method which maintains serum cholesterol concentrations below the level which places an individual at risk for developing adverse health effects associated with elevated lipids such as, but not limited to, coronary artery disease, atherosclerosis and/or arteriosclerosis.

b). "Hypercholesterolemia" means a serum total cholesterol concentration which is significantly higher than the normal level observed for comparable individuals. The concentration indicating hypercholesterolemia is generally greater than about 200 mg/dl, but serum cholesterol concentrations less than about 200 mg/dl may be indicative of hypercholesterolemia, since the reference range for serum cholesterol is age- and gender-dependent.

c). "Substantial homology" means a sequence which retains the biological function of interacting with a regulatory factor capable of regulating expression of the C7αH gene to provide increased synthesis of mRNA even in the presence of dietary cholesterol.

d). "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species which include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

The following examples are offered to illustrate embodiments of the present invention, but should not be read as limiting the scope of the invention.

EXAMPLE 1

Transfection and Library Preparation

Hepatocyte Preparation

NR and CRT rabbits were sacrificed with Nembutal, hepatic tissue removed aseptically, and the liver medial lobe separated from the organ. The medial lobe was cannulated via the largest exposed vessel and perfused with 500 ml of $Ca^{2+}$-free Hank's buffered saline solution (HBS) (GIBCO BRL, Gaithersburg, Md.) at 37° C. The tissue was then perfused with 100 ml of $Ca^{2+}$ replete HBS followed by a solution containing collagenase (400 U/ml) and soybean trypsin inhibitor (1 mg/ml) in media 199 (GIBCO BRL) which was re-circulated with oxygenation for thirty minutes. The digested tissue was placed in a sterile dish, gently teased apart, transferred to centrifuge tubes and therein washed three times in prewarmed media 199. Cells were re-suspended in high-glucose Dulbecco's Minimal Essential Medium (DMEM) (GIBCO BRL) with 10% Fetal Bovine Serum (FBS) and plated. Four hours after plating, the media was changed to Williams media E (GIBCO BRL) supplemented as described by Lanford, et al., "Analysis of plasma protein aaand lipoprotein synthesis in long-term primary cultures of baboon heptacytes maintained in serum-free medium," *In Vitro Cellular Developmental Biology* 25:174 (1989). From a single rabbit, twenty 75 cm² dishes were typically plated. Maintenance of the CRT phenotype in the cultured cells was assessed by measuring HMG-CoA reductase activity, which was markedly elevated in CRT hepatocytes compared to NR cells in the presence of sterol.

Expression Plasmids for Transfection Studies

Rabbit HMG-CoA reductase and human LDL receptor chloramphenicol acetyl transferase (CAT) plasmids were transfected into several other cell lines, including human HepG2 cells and Jurkat cells (obtained from American Type Culture Collection, Rockville, Md.). In addition to HMG-CoA reductase and the LDL receptor, C7αH was a useful marker gene for the resistant phenotype. Two genomic libraries in the vector lambda GEM 12 (Promega Corp., Madison, Wis.) were constructed. The libraries are deposited at the American Type Culture Collection, 12301 Parklawn Drive, Rockville, Md., 20852, USA on Feb. 2, 1993. The libraries are identified as cultures mlo/CRT (A.T.C.C. No. 75410) from the resistant (CRT) phenotype and mlo/crt⁻ (A.T.C.C. No. 75411) from the normal (NR) phenotype.

Genomic DNA was prepared from NR and CRT rabbits using the technique of Miller, et al., "A simple salting out procedure for exacting DNA from human nucleated cells," *Nuc. Acid Res.* 16:1215 (1988), partially digested with Mbo I, ligated into the vector arms, and packaged essentially as described by Stratagene. The libraries were screened with a probe derived from the 5' end of cDNAs from CRT rabbits described below. Clones containing the C7αH promoter were identified by sequence analysis, compared to rat and human C7αH genes, and confirmed by S-1 analysis. The C7αH promoters were cloned into a promoterless CAT-containing plasmid (SV0CAT, available from Promega Corp., Madison, Wis.) and expression assessed following transient transfection into primary fibroblasts or hepatocytes as described below. Approximately 5 kb of 5' flanking sequences in these constructs was used. The mlo/CRT genomic library was used to provide the C7αH core promoter sequences and the C7αH regulatory factor as described in examples 4, 5 and 6 below. The CRT genomic library is also useful for tissue typing and identification of tissue from the CRT phenotype. The expression plasmids, vectors and transformed cells are useful in producing the C7αH regulatory factor.

Hepatocyte Transfection

CAT is used as a marker gene in hepatocytes. Transfections in hepatocytes is accomplished using Lipofectin (GIBCO BRL, Gaithersburg, Md.) as described by the manufacturer. Transfection efficiency is monitored using a β-galactosidase reporter (RSV-βGAL), with the Rous sarcoma virus (RSV) promoter used as an internal control in all experiments. Data is standardized as CAT activity/β-galactosidase activity.

A cis-acting mutation in the CRT C7αH promoter is detected by increased expression of CRT promoter constructs in hepatocytes from both NR and CRT compared to NR constructions. Alternatively, an increase in the expression of any of the marker genes, which is specific to CRT cells compared to NR hepatocytes, indicates the presence of an alteration in an important trans-acting transcription factor in CRT cells. Deletion analysis of the NR or CRT promoter defines elements responsible for the increase in activity and serve as DNA probes for further characterization of such a regulatory factor. Such characterization includes studies on DNA-protein interactions by gel shift analysis and DNase-footprint analysis using the techniques described in Ausubel, F. M., et al. (Eds.) *Current Protocols in Molecular Biology* pg:12.2.1–12.2.7 (1987).

EXAMPLE 2

C7αH Activity

Microsome Preparation

After an overnight fast, age-, sex- and weight-matched pairs of normal and resistant rabbits were anesthetized and killed at 9:00 a.m. The livers were removed, perfused with cold phosphate-buffered saline (PBS), and homogenized on ice in four volumes 0.05 M Tris-acetate, 1 mM EDTA, 1.15% KCl, 50 mM NaF, pH 7.5. All subsequent procedures were performed at 4° C. Cellular debris was pelleted by centrifugation at 10,000×g for 20 minutes. Microsomes were pelleted by centrifugation of the 10,000×g supernatant at 100,000×g for 60 minutes. The microsomal pellet was re-suspended and washed in a volume of 1.15% KCl, 1 mM EDTA, 50 mM NaF equal to that of the supernatant, and collected by centrifugation at 100,000×g for 60 minutes. The final pellet was resuspended in a volume of 100 mM potassium phosphate, 20% glycerol, 0.10 mM EDTA, 5 mM DTT, 50 mM NaF, pH 7.4 equal to 1.5 ml/g of liver homogenized (final concentration was about 30 mg microsomal protein/ml). The microsomes were stored at −20° C. and enzyme activity measured within two weeks of preparation. Microsomal protein concentration was determined by a modified Lowry procedure as described by Peterson. Peterson, G. L., "A Simplification of the Protein Assay Method of Lowry, et al. Which is More Generally Applicable," *Anal. Biochem.* 83:346–356 (1977). Briefly, triplicate aliquots of the microsomal preparation and BSA standards were precipitated with deoxycholate and trichloroacetic acid. The pellet was resuspended in 1 ml water and mixed with an equal volume of 0.025% copper sulfate, 0.05% potassium tartrate, 2.5% sodium carbonate, 0.2 N NaOH and 2.5% sodium dodecyl sulfate (SDS), and incubated at room temperature for 10 minutes. Five hundred microliters of 0.4 Folin-Ciocalteau phenol reagent was added to the samples and mixed immediately. After a 30 minute incubation at room temperature, the absorbance of the samples was measured spectrophotometrically at 750 nm. The microsomal protein concentration was determined by comparison to a bovine serum albumin (BSA) standard curve.

C7αH Activity Measurements

C7αH activity was measured in liver microsomes according to modifications of the method of Chiang, J. Y. L., Miller, W. F., and Lin, G-M., "Regulation of Cholesterol 7α-Hydroxylase in the Liver," *J. Biol. Chem.* 265:3889–3897 (1990). Liver microsomes (2 mg) were incubated in 1 ml of buffer containing 0.10 M potassium phosphate, 50 mM NaF, 5 mM DTT, 0.105% 3-[(3-Cholamidopropyl)-dimethylammonio]-1-propane-sulfonate] (CHAPS, Sigma Chemical Co., St. Louis, Mo.), pH 7.4. Ten microliters of 10 nM cholesterol in 3% Triton X-100 were then added, and the mixture was pre-incubated for five minutes at 37° C. The reaction was initiated by the addition of 100 μl of 12.5 mg/ml NADPH. The samples were incubated at 37° for 30 minutes, and the reaction terminated by adding 30 μl of 20% sodium cholate. 7β-Hydroxycholesterol, 0.5 μg dissolved in ethanol, was added as an internal standard to estimate recovery. The samples were then derivatized by adding 100 μl of cholesterol oxidase (1 unit) in 10 mM potassium phosphate, 1 nM DTT, followed by incubation at 37° C. for 10 minutes. The reaction was terminated by the addition of 2 ml of ethanol, and the samples were extracted three times with 6 ml of petroleum ether. The combined organic phases were dried under nitrogen, and the residue was resuspended in 50 μl of acetonitrile:methanol (85:15). A 10 μl aliquot was separated in acetonitrile:methanol (85:15) with a $C_{18}$ reverse phase HPLC column. The absorbance of the samples was measured at 240 nm. At a flow rate of 1.0 ml/min, the 7α- and 7β-hydroxy-4-cholesten-3-one derivatives eluted between ten and thirteen minutes. Peak areas were converted to product mass by comparison to a standard curve. The endogenous mass of 7α- and 7β-hydroxycholesterol in the microsomal preparations was determined in aliquots of microsomes that were boiled for ten minutes before experimental assay for C7αH activity. The CRT rabbit had a significantly higher C7αH activity than the NR rabbit ($p<0.05$).

EXAMPLE 3

Cloning Rabbit C7αH

Oligonucleotide Synthesis

Five oligonucleotide primers were synthesized according to the rat C7αH cDNA sequence. See, for example, Jelinek, D. F., Anderson, S., Slaughter, C. A., and Russell, D. W., "Cloning and Regulation of Cholesterol 7α-Hydroxylase, the Rate-Limiting Enzyme in Bile Acid Biosynthesis," *J. Biol. Chem.* 265:8190–8197 (1990). The primers consisted of twenty-four to thirty bases of rat C7αH sequence. An additional ten nucleotides were added to the 5' end of each oligonucleotide to provide a BamH I restriction site for subcloning. The oligonucleotides were synthesized in a Cyclone (Milligen/Biosearch, Novato, Calif.) DNA synthesizer and purified over Oligopak (Milligen/Biosearch, Novato, Calif.) columns before amplification.

cDNA Synthesis

Total cellular RNA was isolated by the guanidine isothiocyanate/CsCl method (Chirgwin, J. M., Przybyla, A. E., MacDonald, R. J., and Rutter, W. J., "Isolation of Biologically Active Ribonucleic Acid from Sources Enriched in Ribonuclease," *Biochem.* 18:5294–5299 (1979)) from a normal (NR) and a resistant (CRT) rabbit fed a 0.25% cholesterol-enriched diet for eight weeks. cDNA synthesis was carried out as described by Gibbs, R. A., Nguyen, P-N., McBride, L. J., Koepf, S. M., and Caskey, C. T., "Identification of Mutations Leading to the Lesch-Nyhan Syndrome by Automated Direct DNA Sequencing of In Vitro Amplified cDNA," *Proc. Natl. Acad. Sci. USA* 86:1919–1923 (1989). Briefly, 5 μg liver total RNA was mixed with 10 μg of random hexanucleotides, 20 units of RNAsin and 2 μl deoxynucleoside triphosphates (dNTPs) (25 mM each) in 18.5 μl containing 50 mM Tris-HCl, 8 mM $MgCl_2$, 3 mM KCl, 10 mM dithiothreitol (DTT), pH 8.3 at 37° C. The mixture was heated to 95° C. to denature the RNA and cooled to room temperature. Another 20 units of RNAsin and 15 units of Moloney murine leukemia virus reverse transcriptase (Stratagene, La Jolla, Calif.) were added. The mixture was incubated at 37° C. for 60 minutes and the reaction was terminated by incubation at 95° C. for five minutes.

cDNA Amplification

PCR amplification was performed as described by Gibbs, R. A., Nguyen, P-N., McBride, L. J., Koepf, S. M., and Caskey, C. T., "Identification of Mutations Leading to the Lesch-Nyhan Syndrome by Automated Direct DNA Sequencing of In Vitro Amplified cDNA," *Proc. Natl. Acad. Sci. USA* 86:1919–1923 (1989). Ten percent of the product obtained from the cDNA synthesis reaction (2 μl) was mixed in 99 μl with 1 mM dNTPS, 1 μM each of the 5' and 3' oligonucleotide primers, 6.7 MM $MgCl_2$, 16.6 mM $(NH_2)_2SO_4$, 5 mM β-mercaptoethanol, 67 mM Tris-HCl, 6.8 μM EDTA, 80 μg/ml BSA, pH 8.8 at 25° C. The mixture was denatured at 95° C. for five minutes and cooled to 65° C. Five units of Taq polymerase (Promega Corp., Madison, Wis.) were added, and 50 μl of light mineral oil was overlaid on the samples. The samples were incubated at 65° C. in an Ericomp thermal cycler (Ericomp, San Diego, Calif.) for five minutes and then subjected to 30 cycles of denaturation (94° C., 25 seconds), annealing (50° C., 45 seconds), and polymerization (72° C., two minutes, 10 seconds). The final products were extended at 72° C. for eight minutes.

PCR Product and Analysis

The oligonucleotide primers corresponding to unique regions of the rat C7αH cDNA (Jelinek, D. F., Anderson, S., Slaughter, C. A., and Russell, D. W., "Cloning and Regulation of Cholesterol 7α-Hydroxylase, the Rate-Limiting Enzyme in Bile Acid Biosynthesis," *J. Biol. Chem.* 265:8190–8197 (1990)) were synthesized and used to amplify normal and resistant rabbit liver cDNAs (Gibbs, R. A., Nguyen, P-N., McBride, L. J., Koepf, S. M., and Caskey, C. T., "Identification of Mutations Leading to the Lesch-Nyhan Syndrome by Automated Direct DNA Sequencing of In Vitro Amplified cDNA," *Proc. Natl. Acad. Sci. USA* 86:1919–1923 (1989)). The sequence and designation of these primers were:

primer C7αH-7 (SEQ ID NO: 2):
  5'-GCATGGATCCCCCAAATGATGGAAATACC-3';
primer C7αH-6 (SEQ ID NO: 3):
  5'-GCATGGATCCGGAGCTTTACAGAGTGCTGG-3';
primer C7αH-1 (SEQ ID NO: 4):
  5'-GCATGGATCCGGATGTTATAGGAACCGTCC-3';
primer C7αH-2 (SEQ ID NO: 5):
  5'-GCATGGATCCGGCAAAATTCCCAAGCC-3'; and
primer c7αH-5 (SEQ ID NO: 6):
  5'-GCATGGATCCATGATGACTATTTCTTTGATT TGG-3'.

One primer set, C7αH-7/C7αH-1, produced the expected 800 bp PCR product from both normal and resistant rabbit liver cDNAs.

The 800 bp products obtained from amplification of normal and resistant rabbit liver cDNAs were cloned into a bacterial host vector by standard techniques and sequenced. The alignment of one rabbit C7αH clone, RAB800-55, and a portion of the rat cDNA sequence (Jelinek, D. F., Anderson, S., Slaughter, C. A., and Russell, D. W., "Cloning and Regulation of Cholesterol 7α-Hydroxylase, the Rate-Limiting Enzyme in Bile Acid Biosynthesis," *J. Biol. Chem.* 265:8190–8197 (1990)) was analyzed. At the nucleotide level, the rabbit and rat sequences are 77% identical. The predicted peptide sequences of RAB800-55 and the C7αH cDNA are also 77% identical and, based on conservative amino acid substitutions, 81% homologous. For the 800 bp sequenced thus far, the rabbit C7αH has a three amino acid in-frame deletion relative to the rat peptide sequence.

C7αH mRNA Analysis

A 329 nucleotide rabbit antisense C7αH probe was labeled with [α-$^{32}$P]UTP (3000 Ci/mmol) by in vitro transcription according to the manufacturer's specifications (Promega Corp.)

A 142 bp clone corresponding to the rabbit glyceraldehyde 3-phosphate dehydrogenase (GAPDH) was provided by Dr. P. Schimmel (Putney, S. D., Herlihy, W. C., and Schimmel, P., "A New Troponin T and cDNA Clones for 13 Different Muscle Proteins, Found by Shotgun Sequencing," *Nature* 302:718–721 (1983)). This fragment was subcloned into pSP72 (Promega Corp.), digested at an internal Hinf I restriction site, and transcribed from the SP6 promoter (Riboprobe transcription kit, Promega Corp.) as described above to produce a 132 bp probe.

Total cellular RNA was isolated by the guanidine isothiocyanate/CsCl method (Chirgwin, J. M., Przybyla, A. E., MacDonald, R. J., and Rutter, W. J., "Isolation of Biologically Active Ribonucleic Acid from Sources Enriched in Ribonuclease," *Biochem.* 18:5294–5299 (1979)) from livers of normal and resistant rabbits fed a basal or 0.25% cholesterol-enriched diet for eight weeks.

Ten micrograms of total RNA was denatured in 15 mM methyl-mercuric hydroxide (Alfa Products, Danvers, Mass.) and fractionated on a 0.9% agarose gel in 20% formaldehyde. The RNA was transferred to Duralon membranes (Stratagene, La Jolla, Calif.) and crosslinked to the membrane with UV-light (Stratalinker 1800, Stratagene).

Membranes were hybridized for 18 hours at 60° C. in 50% formamide, 0.8 M NaCl, 50 mM piperazine ethanesulfonic acid (PIPES), 1 mM EDTA with $1\times10^6$ dpm/ml of the cRNA probe. Membranes were washed in 2× standard sodium citrate (SSC), 0.1% SDS for ten minutes at 60° C. Filters were exposed to Hyperfine-MP film (Amersham, Arlington Heights, Ill.) with intensifying screens for two weeks at −80° C. Autoradiograms were quantitated using a BioSearch (Biomed Instruments Inc., Fullerton, Calif.) video densitometer.

As shown in FIG. 1, one predominant transcript of 3.6 kb was present in both the normal (NR) and resistant (CRT) rabbits, and a less abundant transcript of approximately 2.6 kb was also detected in both strains. FIG. 1 depicts the RNA blot of total hepatic mRNA from representative resistant (CRT) and normal (NR) rabbits fed a basal, low-cholesterol diet. Age-, sex- and weight-matched, normal and resistant rabbits were fed either the basal (open bars) or the 0.25% cholesterol-enriched diet (filled bars) for eight to fourteen weeks. Duplicate samples of total cellular RNA were isolated from the livers and hybridized with probes specific for C7αH and GAPDH mRNA. The migration of 18S and 28S ribosomal RNAs are indicated along with the specific C7αH band at 3.6 kilobases.

Figures 2, 2A, 2B:
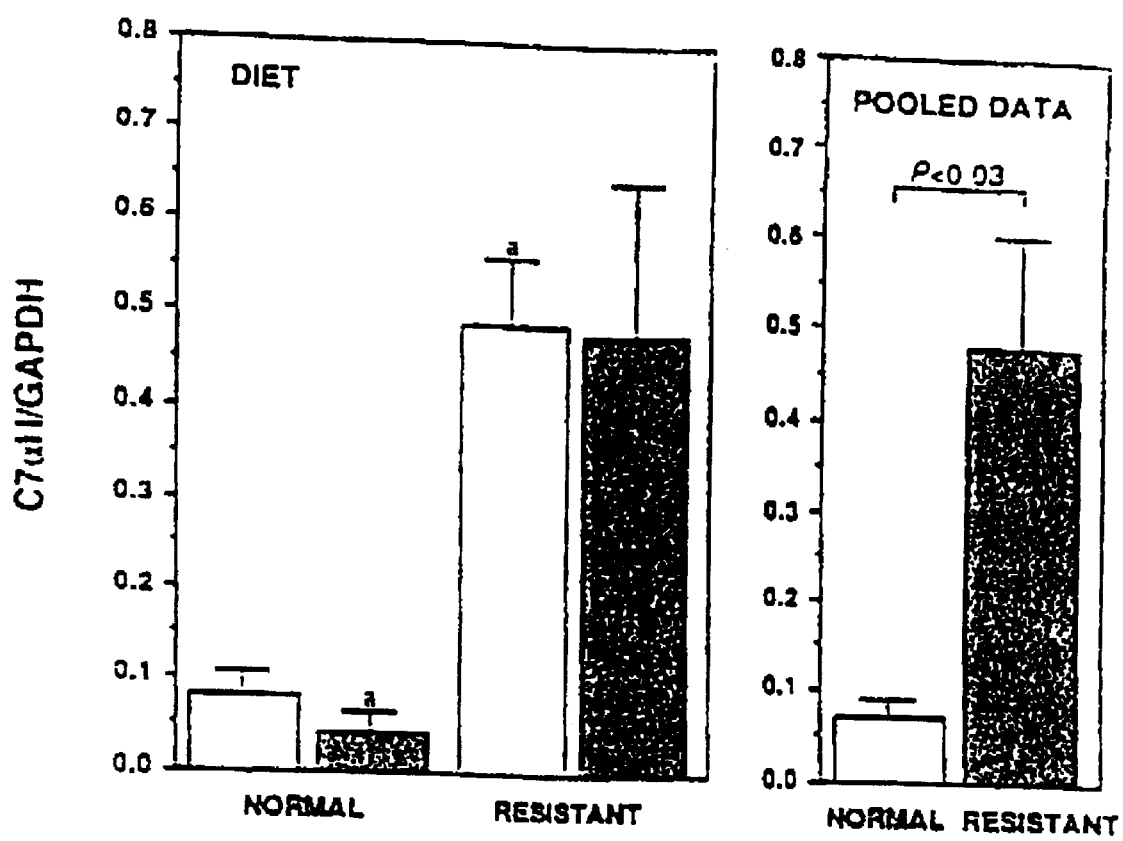
FIG. 2. Depiction of the levels of C7αH in CRT and NR rabbits, normalized to GAPDH.

When fed either the basal or 0.25% cholesterol-enriched diets, the CRT rabbits had higher levels of liver C7αH mRNA as compared to NR rabbits. After hybridization and autoradiography, C7αH and GAPDH mRNA levels were quantitated by laser densitometry. The GAPDH mRNA level was not significantly different between CRT and NR rabbits. Thus, GAPDH mRNA's were used to normalize the observed C7αH mRNA levels. The FIG. 2A data represent the average C7αH mRNA levels, normalized to GAPDH, in each group (mean±SEM or range as denoted by$^a$ in the Figure). The open bars represent the basal diet. The closed bars represent the 0.25% cholesterol-enriched diet. The right panel, FIG. 2B shows combined data (pooled) from normal (open bars, N=7) and resistant (cross-hatched bars, N=7) animals fed either the basal or the 0.25% cholesterol-enriched diets.

The C7αH mRNA/GAPDH mRNA ratios for resistant (CRT) v. normal rabbit (NR) C7αH expression were:

TABLE 1

| C7αH mRNA/GAPDH mRNA | |
|---|---|
| NR: | CRT: |
| 0.0442 | 0.4139 |
| 0.145 | 0.5659 |
| 0.1328 | 1.011 |
| 0.0735 | 0.2067 |
| 0.0117 | 0.1816 |

The lowest CRT to NR mRNA ratio was thus 0.1816/0.145 (1.25) and the highest ratio was 1.011/0.0117 (86.4). Thus, the mRNA increase observed in the CRT rabbits was from 1.25 fold to 86.4 fold, or generally from about 1.25 to about 90 fold.

The data depicted in FIG. 2 and Table 1 show overall, that the CRT rabbits had significantly (P<0.03) higher steady-state C7αH mRNA levels. The increased mRNA levels reflect the increased C7αH expression in the CRT animals. The increased mRNA is due to interaction between the core promoter sequence and the C7αH regulatory factor. The C7αH regulatory factor is derived by expressing sequences of the mlo/CRT library referenced above and isolated as described in Example 5 below. The CRT C7αH regulatory factor causes enhanced cholesterol to bile acid conversion. The enhanced cholesterol to bile acid conversion is maintained, even in the presence of dietary cholesterol. In the NR rabbits, bile acid production decreases more rapidly as dietary-derived cholesterol accumulates.

EXAMPLE 4

C7αH Core Promoter Isolation and Sequence

Phage DNA was isolated and purified by three rounds of CsCl purification as described by Ausbel, F. M., et al. (Eds.) *Current Protocols in Molecular Biology* pg1:13.1–1.13.10 (1987). The purified DNA was restricted with BamH I or Sfi I (which remove insert sequences from lambda GEM12) and analyzed initially by hybridization with an antisense oligomer (45 mers) corresponding to C7αH sequences in exon 1 at nucleotides 84–129. The oligomer is depicted in FIG. 3 (SEQ ID NO: 7). This oligomer was chosen for two purposes: (a) it is highly specific to C7αH and is completely conserved between NR and CRT rabbits, and (b) its location is ideal for use in primer extension analyses. Inserts which hybridized to this oligonucleotide were further analyzed by "one-directional" PCR using the same 45 mer oligonucleotide. Candidate promoter fragments from both NR and CRT rabbit genes were sub-cloned (in pGEM 3zf(+), Promega Corp, Madison, Wis.) and sequenced according to manufacturer's instructions using an Applied Biosystems (Foster City, Calif.) 373A automated DNA sequencer. FIG. 4 depicts the nucleotide sequence from the CRT rabbit C7αH promoter. FIG. 5 shows the sequence homology between the human and rabbit C7αH promoter.

Use of a core promoter (such as the sequence shown in FIG. 4 for the CRT C7αH gene) for the identification of more distal cis-acting sequences and the factors that bind distal sequences, has been established for other P-450 enzymes. For example, 21-hydroxylase, an enzyme of the adrenal cortex, contains sequences within 330 bases of the start of transcription which confer basal and inducible expression (Handler, J. D., Schimmer, B. P., Flynn, T. R., Szyf, M., Rice, B. A., and Parker, K. L., "Regulation of 21-Hydroxylase Expression," *Endocrine Research* 15;31–47, (1989)). Furthermore, sequences between –150 and –330 interact with a factor that allows inducibility by adrenocorticotropic hormone (ACTH).

Similarly, the 17α-hydroxylase gene, which is expressed in gonadal and adrenal tissue, has a core promoter consisting of 245 bases. Using approaches similar to that outlined herein, others have shown that cyclic adenosine monophosphate (cAMP) could induce the 17α-hydroxylase gene by causing a protein to bind to the region between –245 and –346 (Youngblood, G. L., and Payne, A. H., "Isolation and Characterization of the Mouse P450 17α-Hydroxylase/$C_{17-20}$-Lyase Gene (Cyp17): Transcriptional Regulation of the Gene by Cyclic Adenosine 3',5'-Monophosphate in MA-10 Leydig Cells," *Molecular Endocrinology* 6:927–934 (1992)).

Dopamine β-hydroxylase, another P-450 enzyme that is expressed in neuroendocrine tissue, contains a core promoter of approximately 163 bases and a region between 163 and 230 bases which confers inducibility by cAMP and phorbol esters [Shaskus, J., Greco, D., Asnan, L. P., and Lewis, E. J., "A Bifunctional Genetic Regulatory Element of the Rat Dopamine β-Hydroxylase Gene Influences Cell Type Specificity and Second Messenger-Mediated Transcription," *Journal of Biological Chemistry* 267:18821–18830 (1992)).

FIGS. 4 and 4A shows the C7αH core promoter in the CRT rabbit. The C7αH core promoter and sequences at other locations in the mlo/CRT genomic library deposited as noted herein which code for a C7αH expression regulatory factor (s) provide increased C7αH mRNA levels in the CRT animals, and cholesterol to bile acid conversion, even in the presence of high amounts of dietary cholesterol. The C7αH regulatory factor decreases cholesterol's inhibition of cholesterol to bile acid conversion.

EXAMPLE 5

C7αH Regulatory Factor

Specific regions in the C7αH regulator core promoter that contribute to increased expression of C7αH in CRT rabbits are identified, and the C7αH regulatory factor(s) which interact with these regions are determined, using techniques generally known to those skilled in the art. For example, the C7αH regulator factor is identified by using protein-DNA binding methods and isolating sufficient material for identification and cloning.

DNA regions identified in transfection or infection analysis as important for the increased expression in the CRT rabbit are used as probes in gel mobility shift assays using promoters expressed from the mlo/CRT genomic library. Oligonucleotides corresponding to the regions of interest are synthesized with a Milligen Cyclone DNA synthesizer (Novato, Calif.). After annealing the complementary strand, DNA is labeled with [$^{32}$P] ATP and polynucleotide kinase. Specificity in the gel shift pattern is determined by competition with random oligonucleotides and oligonucleotides which correspond to the binding sequence of known transcription factors.

Specific base contacts are assessed using methylation interference assays as described by Ausbel, F. M., et al. (Eds.) *Current Protocols in Molecular Biology* pg:12.3.1–12.3.6 (1987). Two methods are used to perform this assay, either by (a) binding a protein of interest to a radiolabeled fragment, followed by dimethyl sulfate (DMS) methylation and piperidine cleavage, or (b) partial methylation with DMS, binding of the nuclear proteins, and subsequent piperidine cleavage and analysis. In either case, guanine and, to a lesser extent, adenine nucleotides that form specific base contacts with a protein are identified.

The specific region which binds a C7αH regulatory factor is identified, and the nucleotide sequence is used for further purification. A double-stranded oligomer corresponding to the sequence of the binding region is synthesized in high quantity, and multimers of this sequence are created using T4-ligase. This concatamerized oligonucleotide is attached covalently to a solid support such as Sepharose CL-2B (Pharmacia, Stockholm, Sweden). The nuclear extract containing C7αH regulatory factors of interest is passed through a column containing random (calf thymus) DNA to remove non-specific DNA binding proteins and the eluate passed through the oligonucleotide-specific column. Elution of the bound protein is accomplished by increasing the salt concentration in the buffer, generally as described in Montminy, M. P., and Bilezikjian, L. M., "Binding of a nuclear protein to the cyclic-AMP response element of the somatostatin gene," *Nature* 329: 175–178 (1987), and Kadonaga, J. T. and Tjian, R., "Affinity purification of sequence-specific DNA binding proteins," *Proc. Natl. Acad. Sci.* 83: 5889–5893 (1986).

EXAMPLE 6

Alternate Method for Isolating C7αH Regulatory Factor

A biochemical approach as described by Parker and Topol, "A Drosophila RNA polymerase II transcription factor contains a promoter-region-specific DNA-binding activity," *Cell* 36: 357–369 (1984) or Weiderrecht, et al., "The saccharomyces and drosophila heat shock transcription factors are identical in size and DNA binding properties," *Cell* 48: 507–515 (1987) is also used to isolate the C7UH regulatory factor. The mlo/CRT genomic DNA library is amplified and the proteins expressed. The expression products are extracted using 1 M NaCl and concentrated using 30% w/v ammonium sulfate. The precipitate thus obtained is dialyzed against a solution containing 10 mM Tris-HCl, 1 mM ethylenediamine tetraacetic acid (EDTA), and 10 MM $MgCl_2$. This extract is tested for the ability to interact with the C7αH core promoter. Gel-shift analysis is conducted using radio-labelled oligonucleotides corresponding in sequence to the C7αH regulatory factor binding region. Enrichment of the C7αH regulatory factor to homogeneity is accomplished using classical biochemical approaches.

Initial enrichment employs DEAE-ion exchange chromatography with fractions of the extract eluted with increasing concentrations of NaCl. Fractions containing active C7αH regulatory factor as determined by the gel-shift analysis are further purified using heparin Sepharose (Pharmacia) affinity chromatography and purified to homogeneity using Sephadex (Pharmacia) molecular sieving chromatography.

EXAMPLE 7

Comparison of C7αH Regulatory Factor to HNF-3

Studies on the human C7αH promoter have implicated a factor called HNF-3 as participating in transcriptional regulation of the C7αH gene. The C7αH regulatory factor in CRT rabbits is not HNF-3. This conclusion is supported by two lines of evidence. One, direct RNA analysis of liver RNA from normal and CRT rabbits, has indicated that while an mRNA for HNF-3 is present, it is expressed at the same level in normal and CRT rabbits, and this level does not change upon cholesterol challenge. Secondly, HNF-3 is a non-specific transcriptional regulator in that a number of liver genes, notably those coding for albumin and the kininogens, are affected by this factor. Expression of these other genes is identical in NR and CRT rabbits, indicating that HNF-3 is not the factor that is different in the CRT rabbits.

EXAMPLE 8

Compounding the C7αH Regulatory Factor with a Carrier

The C7αH regulatory factor isolated as described in Example 5 or 6 is compounded with a suitable carrier known to those skilled in the art as acceptable for delivery of the C7αH regulatory factor. The nature of these carriers is predicated on the chemical nature of the C7αH regulatory factor, as is well known to those having ordinary skill in the art. The dosage is selected to produce the desired cholesterol level in serum, preferably less than 250 mg/dl, more preferably less than 200 mg/dl of serum cholesterol in humans. The dosage may also be monitored by a C7αH mRNA level increase. The effective dose will produce increased C7αH mRNA of about 1.25 to about 90 fold, preferably about 2.0 to about 25 fold, more preferably about 5 to about 10 fold increases over levels observed prior to administration of the regulatory factor.

EXAMPLE 9

Administration of the C7αH Regulatory Factor

The C7αH regulatory factor isolated as described in Example 5 or 6 is administered to humans. The C7αH regulatory factor is administered to those individuals at high, or moderate, risk of developing hypercholesterolemia and/or coronary artery disease. The C7αH regulatory factor is also administered prophylactically to individuals to prevent the onset of hypercholesterolemia and/or coronary artery disease. The C7αH regulatory factor is administered by mechanisms which deliver it to tissues which regulate the expression of cholesterol metabolizing enzyme(s) such as C7αH. The C7αH regulatory factor is administered in a dose sufficient to increase C7αH mRNA levels in the range of from about 1.25 to about 90 fold, preferably about 2 to about 25 fold, most preferably about 5 to about 10 fold over C7αH mRNA levels observed in the absence of administered C7αH regulatory factor. Alternatively, the regulatory factor is administered in a dose sufficient to achieve reduction in the level of serum cholesterol, preferably to below about 250 mg/dl, more preferably to below about 200 mg/dl in a human.

Alternatively, cholesterol control is affected by removing cells from the individual to be treated, transfecting the cells with the DNA sequence of the C7αH regulatory factor that binds to the sequence of SEQ ID NO: 8, or substantial homologs thereof, or mixtures thereof, and replacing the transfected cells back into the individual.

EXAMPLE 10

Use as a Diagnostic

The sequence that codes for the C7αH regulator can be used as a diagnostic for assessing risk of developing hypercholesterolemia and/or coronary artery disease. The sequence coding for the C7αH regulatory is isolated and compared to the sequence found in normal and at-risk individuals.

Alternatively, the C7αH regulatory factor is used in a diagnostic assay. The C7αH regulatory factor is measured in tissue and/or body fluids using standard analytical techniques.

Many other variations and modifications may be made in the techniques herein before described, by those having experience in this technology, without departing from the concept of the present invention. Accordingly, it should be clearly understood that the methods described in the foregoing description are illustrative and not intended as a limitation on the scope of the invention.

EXAMPLE 11

Functional Analysis of the Rabbit Cholesterol 7α-Hydroxylase Promoter in Human Cells The activity of the rabbit cholesterol 70α-hydroxylase promoter was assessed by transfection into human hepatoma cells. Two promoter constructs have been tested: the longest (−1118) contains nucleotides 342 to 1474 of the described sequence and the shorter (−188) contains nucleotides 1229 to 1474. With respect to the start site of transcription, these fragments are −1118 to +55 and −188 to +55 respectively. These fragments were produced by PCR from the rabbit cholesterol 7α-hydroxylase gene such that the 5'-end included an Asp718 restriction site and the 3'-end contained a BamHI restriction site.

These fragments were isolated and ligated into a plasmid, pGL2Basic (Promega Corp., Madison, Wis.), that contains a luciferase reporter gene. This plasmid was digested with Asp718 and BgIII and the above fragments, which have ends compatible with the ends engineered into the fragments, were ligated together using standard methodology.

Human HepG2 cells, a hepatoma cell line, were grown at 37° C. in a humidified 5% $CO_2$ atmosphere on DMEM (Gibco Laboratories, Santa Clara, Calif.) containing 10% fetal bovine serum (Hyclone, Logan, Utah). Cells were subcultured weekly at a 1:3 ratio in 100 mm Falcon tissue culture dishes (Falcon, Oxnard, Calif.). For transfection studies, cells were seeded at 50% confluency into 60 mM Falcon dishes and transfected the next day.

Transfections were performed by calcium phosphate precipitation using the reagents in the Transfection MBS kit from Stratagene (La Jolla, Calif.). DNA was precipitated according to the manufacture's instructions and added dropwise onto each plate. DNA (7.5, 15 or 50µ) of either of the rabbit cholesterol 7α-hydroxylase fragments or control DNA (just the pGL2Basic plasmid) was added to separate plates. After 3 h at 37° C., fresh media was added to each plate. Cells were harvested and lysates prepared 24 hours after transfection.

Expression and function of the transfected DNA was assessed using a standard luciferase assay and a Monolight 2000 luminometer (Analytical Luminenence Laboratories). The protein concentration of the lysates was determined using Pierce BCA Protein Assay kit (Pierce, Rockford, Ill.). Data are expressed as relative light units per mg lysate protein.

The results, illustrated in FIG. 6, show that the rabbit promoter sequences are functional in human cells.

What is claimed is:

1. A DNA fragment comprising the sequence of the rabbit C7αH core promoter.

2. A DNA fragment according to claim 1 wherein the rabbit C7αH core promoter has the sequence of SEQ ID NO: 8.

3. A transformed cell comprising the DNA sequence of the rabbit C7αH core promoter.

4. A transformed cell according to claim 3 wherein the rabbit C7αH core promoter has the sequence of SEQ ID NO: 8.

5. A vector comprising the DNA sequence of the rabbit C7αH core promoters.

6. A vector according to claim 5 wherein the rabbit C7αH core promoter has the sequence of SEQ ID NO: 8.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 217 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: ORYCTOLAGUS CUNICULUS
      (B) STRAIN: NR
      (D) DEVELOPMENTAL STAGE: MATURE
      (F) TISSUE TYPE: HEPATIC (xi) SEQUENCE DESCRIPTION: SEQ ID NO:1:

```
GATAATACCA CTATCTTTTT TTTCCTAATA GGATGAACAC ATGGTTAATT GTTTGCTTTG      60

GTCACTCAAG TTCAAGTTAT TGAATCAGGG TCCTACGTAT ATAAAAACTC TAGCTTCAGA     120

CTGTTCAGAG ACACCCTTGC CTTTCTAATC ATAGATTCTC CCTGTCAGGA GTTTTACAGA     180

TTTGCGAAAT GATTACCATA TTTTGGATCT GGGGGGG                              217
```

(2) INFORMATION FOR SEQ ID NO:2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GCATGGATCC CCCAAATGAT GGAAATACC                                        29
```

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
GCATGGATCC GGAGCTTTAC AGAGTGCTGG                                       30
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCATGGATCC GGATGTTATA GGAACCGTCC                                    30

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCATGGATCC GGCAAAATTC CCAAGCC                                       27

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCATGGATCC ATGATGACTA TTTCTTTGAT TTGG                               34

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TAGTCCCAGA ATAAGCCACA AACAACAGCA CACTGATAGA CATAT                   45

(2) INFORMATION FOR SEQ ID NO:8:

(i) SEQUENCE CHARACTERISTICS:
        (A) LENGTH: 1876 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: ORYCTOLAGUS CUNICULUS
        (B) STRAIN: NR
        (D) DEVELOPMENTAL STAGE: MATURE

```
       (F) TISSUE TYPE: HEPATIC (xi) SEQUENCE DESCRIPTION: SEQ ID NO:8:

ATATTTTAAG TTTCATTTTT TCCCTGAGTT TTTTTTGTTG AAGTATTGCA ATATGTGTGT     60

GTGTGTGTGT GTAATAAGAA TGTATACATC TCCAGAGCAT GATACTACTG CCCTTCAAAC    120

CCACAAAGTC TTTAATATAA CCTCATATTT GTGCATGTGT TTATATGTCA GTCATCTAAC    180

CCCGTGTTGT CAGATTCAGG GGTCATTTTT GATCCTCTTA CTTGACCTCG GAGTAGCATG    240

TGATATAGTT CACTCATCTT CCTTCTGCTC TGGCTTTCTG TACCATGATA TCATCTGCAT    300

TTTCTTCCTG ACTCTCATTA TCTTCCTCCT CACCTTGGAC TGATCTCCCC GAGTGAAGTG    360

TCTGTGGCCT GGGTTGAATT CTGTTTCTTT CTTTGATCTT TCTTTCTCCC TAAGTGATTT    420

CATAGGACCT CTTGGCTTTA AATACCATCC AAATGCTGGT GAATTGATAT TTATATCTCC    480

AACTCTAGCC TTTCTCCTTC ACTTTAGACT CACTCAATTG TCAACTTGAC ATTGACCCGA    540

TGGTTCCTAA AAGATCTCCC AAACATCATA TGTCCAAAAT AGTATTCTGA TGTATTGCCT    600

TCCAAGACCT CTCTCCCTGC TCACAAGCAA TTCTGTATGA ATTGTTTCTT ATCTAACTTT    660

TTGTGGTTTT AATCTTAGGT AACTTTGTCG GATTCACTCT GCTCCAGTTA GTTGTACTAA    720

ATTTTCCAGT TAGTAGATGT ACAAAGTTTA TGTTTGAAAT GAGGTGGGTT TCTTTAATAA    780

ATAGAAAAAT TAATAAACAA ATTTAAGGTA TAAAAAAGTT TGATAATGTT TTTATGCTTA    840

AAAGAAACTG TTTTATTTAC TTTCTTGATA CTAGGTGAGT AATATGTTAT GATCTATGTA    900

AATTGTCTAT GATTTTGGAA AAATACTGAG ACTTGAAGCA AGAGAATCTA GTTCTCTTCC    960

CTTTGAACTT AACCATTGGA TCTCTCTGGC ATTTAAATTA ATTTCTTCTT CAAAATGTAA   1020

TAAGATAAAA AAAGCAACAA GATCAAATCA CTAGTTTGAT GAATAATTTA TACTTAGTTT   1080

TCTTTATGTG TTACATATTT ACTACATATG TTCATCTTGA ACAGATTTGT TTTTATACAC   1140

ATACCTAACT TGTAATACTA GCTGCTGTCC CCAGGAATGA ATGTTGAGTC AACATATGTT   1200

TGAGAGACCT TCAACTTATC AAGTATTGCA GGTTTCTGAT TGTTTTGGAA GATCTTCTGA   1260

TGCCTGTGGA CTTAGTTCAA GGCTAGTTAA TACCACTATC TTTTTTTTCC TAATAGGATG   1320

AACAAATGGT TAATTGTTTG CTTTGGTCAC TCAAGTTCAA GTTATTGAAT CAGGGTCCTA   1380

CGTATATAAA AACTCTAGCT TCAGACTGTT CAGAGACACC CTTGCCTTTC TAATCATAGA   1440

TTCTCCCTGT CAGGAGTTTT ACAGATTTGC GAAATGATTA CCATATTTGG ATCTGGGGGA   1500

TATGTCTATC AGTGTGCTGT TGTTTGTGGC TTATTCTGGG ACTAAGGAGA AGGTAAGGAA   1560

AGTTTTGTTT ATGTTAAATT ACCTTTTAGT TGTTTCATTT AATGTTCTTT TTCCTCTACT   1620

GTATAATAAG TTTGGTTTCC CATACTTACA TATATCTGCA TTTTCTTCTT CATTTTAAAC   1680

TACTGATTTC ATTCAAACAA ATTGATATAT TTTGACTATA ACAAAGCATT TGGCAGGTTC   1740

CTTTTTTAAA ATTGACATAT ACTAATGTAA TGTATAAATG TGTACATTTG TTAACTATGA   1800

TTGATGGAAA TTTCATAAGA TCCCTGTATG TGTTTACGTG TCTATGTACA AAAAAAGCTC   1860

GGATTAGGAA GGATCC                                                  1876
```